United States Patent [19]

Fest et al.

[11] 4,080,444
[45] Mar. 21, 1978

[54] O-ALKYL-O-(N,N-DIMETHYLFOR-MAMIDINO)-PHENYLTHIONOPHOS-PHONIC ACID DIESTERS AND METHOD OF COMBATING ARTHROPADS

[75] Inventors: Christa Fest, Wuppertal; Ingeborg Hammann, Cologne, both of Germany

[73] Assignee: Bayer Aktiengesellschaft, Leverkusen, Germany

[21] Appl. No.: 750,349

[22] Filed: Dec. 13, 1976

[30] Foreign Application Priority Data

Dec. 18, 1975 Germany ............................. 2556961

[51] Int. Cl.$^2$ ........................... A01N 9/36; C07F 9/40
[52] U.S. Cl. ..................................... 424/211; 260/945
[58] Field of Search ................. 260/945, 944; 424/211

[56] References Cited
FOREIGN PATENT DOCUMENTS 987,381  3/1965  United Kingdom.

OTHER PUBLICATIONS
Derkach et al. "Chemical Abstracts", vol. 58, p. 2388.

*Primary Examiner*—Anton H. Sutto
*Attorney, Agent, or Firm*—Burgess, Dinklage & Sprung

[57] ABSTRACT

O-Alkyl-O-(N,N-dimethylformamidino)-phenylthionophosphonic acid diesters of the formula

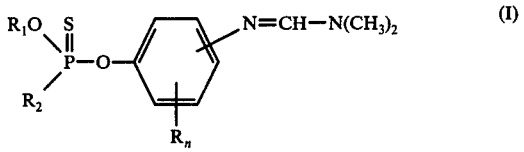

in which
 $R_1$ is alkyl with 1 to 6 carbon atoms,
 $R_2$ is alkyl with 1 to 6 carbon atoms or phenyl,
 R each independently is a halogen atom or a nitro group, and
$n$ is 0, 1, 2, 3 or 4, which possess arthropodicidal properties.

9 Claims, No Drawings

O-ALKYL-O-(N,N-DIMETHYLFORMAMIDINO)-PHENYLTHIONOPHOSPHONIC ACID DIESTERS AND METHOD OF COMBATING ARTHROPADS

The present invention relates to and has for its objects the provision of particular new O-alkyl-O-(N,N-dimethylformamidino)-phenylthionophosphonic acid diesters which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It has been disclosed in U.S. Patent Specification No. 3,459,836 that certain O-alkyl-O-phenylthionophosphonic acid esters, for example O-ethyl-O-(4-bromo-2,5-dichloro-phenyl)thionophenylphosphonic acid ester (Compound A), have insecticidal properties.

The present invention now provides, as new compounds the O-alkyl-O-phenylthionophosphonic acid esters of the general formula

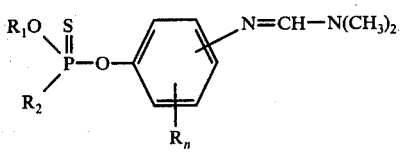

in which
$R_1$ is alkyl with 1 to 6 carbon atoms,
$R_2$ is alkyl with 1 to 6 carbon atoms or phenyl,
R each independently is a halogen atom or a nitro group, and
n is 0, 1, 2, 3 or 4, Preferably, $R_1$ represents straight-chain or branched alkyl with 1 to 4 carbon atoms, $R_2$ represents straight-chain or branched alkyl with 1 to 4 carbon atoms or represents phenyl, R represents chlorine or a nitro group and n represents 0, 1 or 2.

Surprisingly, the O-alkyl-O-phenylthionophosphonic acid esters according to the invention exhibit a better insecticidal action than the corresponding compounds of analogous structure and of the same type of action, previously known from the state of the art. The compounds according to the present invention thus represent a genuine enrichment of the art.

The present invention also provides a process for the preparation of an O-alkyl-O-phenylthionophosphonic acid ester of the general formula (I) in which a phenol of the general formula

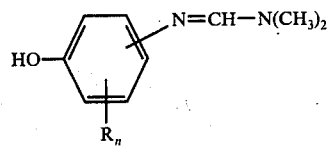

in which
R and n have the abovementioned meanings, is reacted, as such in the presence of an acid acceptor or in the form of an alkali metal salt, alkaline earth metal salt or ammonium salt thereof, with an O-alkyl-thionophosphonic acid ester halide of the general formula

in which
$R_1$ and $R_2$ have the abovementioned meanings and Hal represents halogen, preferably chlorine, if appropriate in the presence of a solvent or diluent.

If, for example, O-n-propylthionoethanephosphonic acid ester chloride and 3-chloro-4-(N,N-dimethylformamidino)-phenol are used as starting materials, the course of the reaction can be represented by the following equation:

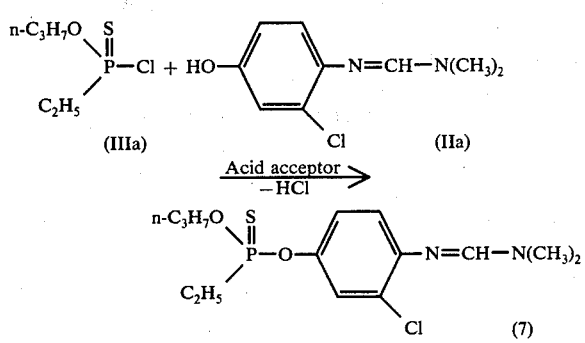

The phenols (II) to be used as starting materials are known from the literature and can be prepared in accordance with generally customary processes (according to German Published Specification DAS No. 1,169,194), as can the O-alkyl-thionophosphonic acid ester halides (III).

The following may be mentioned as individual examples of the phenols (II): 2-(N,N-dimethylformamidino)-phenol, 4-chloro-2-(N,N-dimethylformamidino)-phenol, 4-chloro-2-(N,N-dimethylformamidino)-5-nitro-phenol and 3-chloro-4-(N,N-dimethylformamidino)-phenol.

The following may be mentioned as individual examples of the O-alkylthionophosphonic acid ester halides (III): O-methyl-, O-ethyl-, O-n-propyl-, O-isopropyl-, O-n-butyl-, O-sec.-butyl-, O-isobutyl- and O-tert.-butyl-thionophenylphosphonic acid ester chloride, and also O-methyl-methane-, O-methyl-ethane, O-methyl-n-propane-, O-methyl-isopropane-, O-methyl-n-butane-, O-methyl-sec.-butane-, O-methyl-isobutane-, O-methyl-tert.-butane-, O-ethyl-methane-, O-ethyl-ethane-, O-ethyl-n-propane-, O-ethyl-isopropane-, O-ethyl-n-butane-, O-ethyl-sec.-butane-, O-ethyl-isobutane-, O-ethyl-tert.-butane-, O-n-propyl-methane-, O-n-propyl-ethane-, O-n-propyl-n-propane-, O-n-propyl-isopropane-, O-n-propyl-n-butane-, O-n-propyl-sec.-butane, O-n-propyl-isobutane-, O-n-propyl-tert.-butane-, O-isopropyl-methane-, O-isopropyl-ethane-, O-isopropyl-n-propane-, O-isopropyl-iso-propane, O-isopropyl-n-butane-, O-isopropyl-sec.-butane-, O-isopropyl-isobutane-, O-isopropyl-tert.-butane-, O-n-butyl-methane-, O-n-butyl-ethane-, O-n-butyl-n-propane-, O-n-butyl-isopropane-, O-n-butyl-n-butane-, O-n-butyl-sec.-butane-, O-n-butyl-isobutane-, O-n-butyl-tert.-butane, O-isobutyl-methane-, O-isobutyl-ethane-, O-isobutyl-n-propane-, O-isobutyl-isopropane-, O-isobutyl-n-butane-, O-isobutyl-sec.-butane-, O-isobutyl-isobutane-, O-isobutyl-tert.-butane-, O-sec.-butyl-methane-, O-sec.-butylethane-, O-sec.-butyl-n-propane-, O-sec.-butyl-isopropane-, O-sec.-butyl-n-butane-, O-sec.-butyl-sec.-butane-, O-sec.-butyl-isobutane-, O-sec.-butyl-tert.-butane-, O-tert.-butyl-methane-, O-tert.-butyl-ethane-, O-tert.-butyl-n-propane-, O-tert.-butyl-isopropane-, O-tert.-butyl-n-butane-, O-tert.-butyl-sec.-butane-, O-tert.-butyl-isobutane- and O-tert.-butyl-tert.-butane-thionophosphonic acid ester chloride.

The process for the preparation of the compounds according to the invention is preferably carried out in the presence of a suitable solvent or diluent. Practically all inert organic solvents can be used for this purpose, especially aliphatic and aromatic, optionally chlorinated, hydrocarbons such as benzene, toluene, xylene, benzine, methylene chloride, chloroform, carbon tetrachloride or chlorobenzene; or ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 150° C, preferably at 40° to 70° C.

In general, the reaction is allowed to take place under normal pressure.

To carry out the process, the starting materials are preferably employed in equimolar amounts. An excess of one or other component in general produces no significant advantages. Preferably, the phenol (II) and the acid acceptor, if appropriate in a solvent, are taken and the thionophosphonic acid ester halide (III) is added dropwise. After completion of the reaction, in most cases at an elevated temperature, the mixture is filtered, diluted with water and extracted by shaking with an organic solvent. The organic phase is worked up in the usual manner by drying and distilling off the solvent. The compounds can be purified by redissolving them, precipitating them as the hydrochlorides and subsequently again decomposing the latter.

The new compounds are obtained in the form of oils which in most cases cannot be distilled without decomposition but can be freed from the last volatile constituents by so-called "slight distillation", that is to say by prolonged heating under reduced pressure at moderately elevated temperatures, and can be purified in this way. They are characterized by the refractive index.

As already mentioned, the O-alkyl-O-phenylthionophosphonic acid esters according to the invention are distinguished by an excellent insecticidal activity and are active against plant pests and pests harmful to health. They possess low phytotoxicity and a good action against both sucking and biting insects. Some of the compounds also exhibit a fungicidal and bactericidal activity.

For the reason, the compounds according to the invention can be employed successfully as pesticides in plant protection and in the hygiene field.

The active compounds are well tolerated by plants, have a favorable level of toxicity to warm-blooded animals, and can be used for combating arthropod pests, especially insects and arachnids which are encountered in agriculture, in forestry, in the protection of stored products and of materials, and in the hygiene field. They are active against normally sensitive and resistant species and against all or some stages of development. The abovementioned pests include:

from the class of the *Isopoda*, for example *Oniscus asellus, Armadillidium vulgare* and *Porcellio scaber;* from the class of the *Diplopoda*, for example, *Blaniulus guttulatus;* from the order of the *Chilopoda*, for example *Geophilus carpophagus* and *Scutigera* spec.; from the class of the *Symphyla*, for example *Scutigerella immaculate;* from the order of the *Thysanura*, for example *Lepisma saccharina;* from the order of the *Collembola*, for example *Onychiurus aramatus;* from the order of the *Orthoptera*, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the *Dermaptera*, for example *Forficula auricularia;* from the order of the *Isoptera*, for example *Reticulitermes* spp.; from the order of the *Anoplura*, for example *Phylloxera vastatrix, Pemphigus* spp., *Pediculus humanus corporis, Haematopinus* spp. and *Linognathus* spp.; from the order of the *Mallophaga*, for example *Trichodectes* spp. and *Damalinea* spp.; from the order of the *Thysanoptera*, for example *Hercinothrips femoralis* and *Thrips tabaci;* from the order of the *Heteroptera*, for example *Eurygaster* spp., *Dysdercus intermedius, Piesma quadrata, Cimex lectularius, Rhodnius prolixus* and *Triatoma* spp.; from the order of the *Homoptera*, for example *Aleurodes brassicae, Bemisia tabaci, Trialeurodes vaporariorum, Aphis gossypii, Brevicornye brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.; from the order of the *Lepidoptera*, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., Anthrenus spp., *Attagenus* spp., *Lyctus* spp., Meligethes aeneus, Ptinus spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the *Hymenoptera*, for example *Diprion* spp. *Hoplocampa* spp., *Lasius* spp.; *Monomorium pharaonis* and *Vespa* spp.; from the order of the *Diptera*, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., Bibio hortulanus, Oscinella frit, Phorbia spp., *Pegomyia hyoscayami, Ceratitis capitata, Dacus oleae* and *Tipula paludosa*: from the order of the *Siphonaptera;* for example *Xenopsylla cheopis* and *Ceratophyllus* spp.; from the order of the *Arachnida,* for example *Scorpio maurus* and *Latrodectus mactans;* from the order of the *Acarina,* for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Byrobia praetiosa, Panonychus* spp. and *Tetranychus* spp.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground naturally minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0000001-100, preferably 0.01-10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods, and especially insects, which comprises applying to at least one of correspondingly (a) such arthropods and (b) the corresponding habitat thereof, i.e. the locus to be protected, e.g. to a growing crop, to an area where a crop is to be grown or to a domestic animal, a corresponding combative or toxic amount, i.e. an arthropodicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, with limitation, by the following examples:

EXAMPLE 1

Drosophila test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% meant that all the flies were killed; 0% meant that no flies were killed.

The active compounds, the concentrations of the active compounds, the evaluation times and the results can be seen from the following table:

Table 1

(*Drosophila* test)

| Active compound | Active compound concentration in % | Degree of destruction in % after 1 day |
|---|---|---|
| (structure with Cl, Br, Cl on benzene ring, O—P(=S)(OC$_2$H$_5$)—phenyl) (known) (A) | 0.1<br>0.01 | 95<br>0 |
| (CH$_3$)$_2$N—CH=N—(benzene ring with Cl)—O—P(=S)(CH$_3$)(OC$_2$H$_5$) (2) | 0.1<br>0.01 | 100<br>90 |

EXAMPLE 2

Phaedon larvae test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassicae oleracea*) were sprayed with the preparation of the active compound until dripping wet and were then infested with mustard beetle larvae (*Phaedon cochleariae*).

After the specified periods of time, the degree of destruction was determined in %: 100% meant that all the beetle larvae had been killed, whereas 0% meant that none of the beetle larvae had been killed.

The active compounds, the concentrations of the active compounds, the evaluation times and the results can be seen from the following table:

Table 2
(Phaedon larvae test)

| Active compound | Active compound concentration in % | Degree of destruction in % after 3 days |
|---|---|---|
| 2-bromo-4,5-dichlorophenyl derivative (known) (A) | 0.1 | 100 |
| | 0.01 | 50 |
| | 0.001 | 0 |
| $(CH_3)_2N-CH=N-$ aryl phosphonate (1) | 0.1 | 100 |
| | 0.01 | 100 |
| | 0.001 | 50 |

EXAMPLE 3

Myzus test (contact action)
Solvent: 3 parts by weight of acetone
Emulsifier: 1 part by weight of alkylarylpolyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% meant that all the aphids were killed, whereas 0% meant that none of the aphids were killed.

The active compounds, the concentrations of the active compounds, the evaluation times and the results can be seen from the following table:

Table 3
(*Myzus* test)

| Active compound | Active compound concentration in % | Degree of destruction in % after 1 day |
|---|---|---|
| (known) (A) | 0.1 | 0 |
| (2) | 0.1 | 100 |
| (3) | 0.1 | 100 |
| (1) | 0.1 | 80 |

The process of the present invention is illustrated by the following preparative examples:

EXAMPLE 4 a)

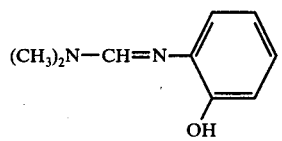

109 g (1 mole) of 2-aminophenol were dissolved in 250 ml of dimethylformamide and 92 ml of phosphorus oxychloride were added while cooling with ice (temperature up to 60° C). The reaction mixture was allowed to finish reacting and 1 liter of ethanol was added, while cooling. The mixture was then stirred for a further hour at room temperature. The resulting hydrochloride was filtered off, rinsed, dried and weighed. To obtain the free base, the compound was dissolved in water and the equivalent amount of sodium carbonate was added. The desired product precipitated and was recrystallized from isopropanol after drying. 68 g (41% of theory) were obtained.

b)

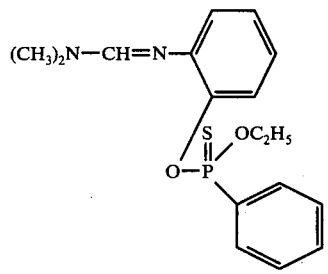
(1)

A mixture of 33 g (0.2 mole) of 2-(N,N-dimethylformamidino)-phenol dissolved in 400 ml of acetonitrile and 56 g (0.2 mole) of potassium carbonate was warmed to 50° C for 1 hour and 44 g (0.2 mole) of O-ethyl-phenylthionophosphonic acid ester chloride were then added. The reaction mixture was kept at 50° C for a further 2 hours, stirred further overnight at room temperature, filtered to remove the alkali metal chloride which had separated out, diluted with water and taken up in chloroform. The chloroform phase was separated off, dried and concentrated. The residue was taken up in ether and hydrogen chloride was passed into the solution. The resulting hydrochloride was filtered off, neutralized with aqueous sodium hydroxide solution and extracted with chloroform. The extract was washed until a neutral reaction was obtained, and was then concentrated, and the residue was subjected to slight distillation. 21 g (30% of theory) of O-ethyl-O-[2-(N,N-dimethylformamidino)-phenyl]-thionophenylphosphonic acid diester were obtained as a clear oil.

The following compounds were prepared by analogous methods:

| Compound No. | Structure | Physical data (melting point, ° C; refractive index) | Yield (% of theory) |
|---|---|---|---|
| 2 | (CH₃)₂N—CH=N—[ring-Cl]—O—P(=S)(CH₃)(OC₂H₅) | $n_D^{23}$: 1.5894 | 72 |
| 3 | (CH₃)₂N—CH=N—[ring-Cl]—O—P(=S)(C₂H₅)(OC₂H₅) | $n_D^{23}$: 1.5789 | 90 |
| 4 | (CH₃)₂N—CH=N—[ring-Cl,NO₂]—O—P(=S)(OC₂H₅)(C₆H₅) | 91 | 69 |

Other compounds which could be similarly prepared include:

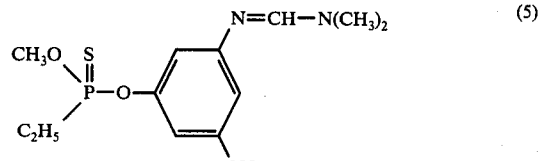
(5)

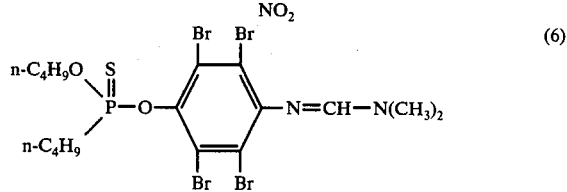
(6)

and the like.

It will be appreciated that the instant specification and examples are set forth by way of illustration and not limitation, and that various modifications and changes may be made without departing from the spirit and scope of the present invention.

What is claimed is:

1. An O-alkyl-O-(N,N-dimethylformamidino)-phenylthionophosphonic acid diester of the formula

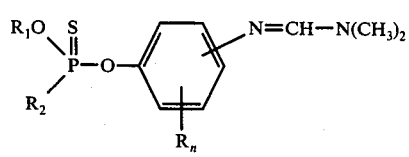

in which

R₁ is alkyl with 1 to 6 carbon atoms, $R_2$ is alkyl with 1 to 6 carbon atoms or phenyl, R each independently is a halogen atom or a nitro group, and n is 0, 1 or 2.

2. A method of combating arthropods which comprises applying to the arthropods or to a habitat thereof an arthropodicidally effective amount of a compound according to claim 1.

3. The method according to claim 2 in which said compound is O-ethyl-O-[2-(N,N-dimethylformamidino)-phenyl]-thionophenylphosphonic acid diester, O-ethyl-O-[3-chloro-4-(N,N-dimethylformamidino)-phenyl]-thionomethanephosphonic acid diester, O-ethyl-O-[3-chloro-4-(N,N-dimethylformamidino)-phenyl]thionoethanephosphonic acid diester, or O-ethyl-O-[4-chloro-2-(N,N-dimethylformamidino)-5-nitro-phenyl]-thionophenylphosphonic acid diester.

4. An arthropodicidal composition containing as active ingredient an arthropodicidally effective amount of a compound according to claim 1 in admixture with a diluent.

5. An ester according to claim 1, in which $R_1$ is alkyl with 1 to 4 carbon atoms, $R_2$ is alkyl with 1 to 4 carbon atoms or phenyl, R each independently is a chlorine atom or a nitro group.

6. The ester according to claim 1 wherein such ester is O-ethyl-O-[2-(N,N-dimethylformamidino)-phenyl]-thionophenylphosphonic acid diester of the formula

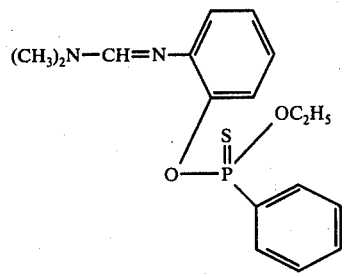

7. The ester according to claim 1 wherein such ester is O-ethyl-O-[3-chloro-4-(N,N-dimethylformamidino)-phenyl]-thionomethanephosphonic acid diester of the formula

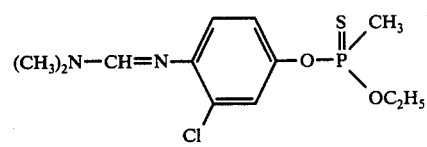

8. The ester according to claim 1 wherein such ester is O-ethyl-O-[3-chloro-4-(N,N-dimethylformamidino)-phenyl]-thionoethanephosphonic acid diester of the formula

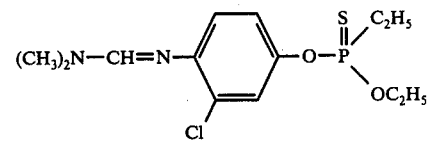

9. The ester according to claim 1 wherein such ester is O-ethyl-O-[4-chloro-2-(N,N-dimethylformamidino)-5-nitro-phenyl]-thionophenylphosphonic acid diester of the formula

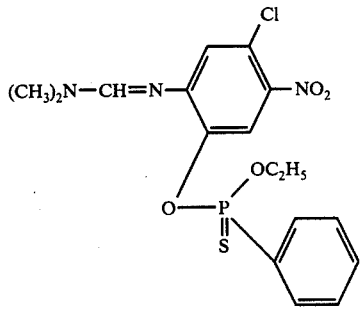

* * * * *